United States Patent [19]

Reichl

[11] 4,315,741
[45] Feb. 16, 1982

[54] HAND-OPERATED INSTRUMENT FOR DENTAL CARE OR TOOTH TREATMENT

[75] Inventor: Ernst Reichl, Munich, Fed. Rep. of Germany

[73] Assignee: Bosch-Siemens Hausgeräte GmbH, Stuttgart, Fed. Rep. of Germany

[21] Appl. No.: 111,327

[22] Filed: Jan. 11, 1980

[30] Foreign Application Priority Data

Jan. 12, 1979 [DE] Fed. Rep. of Germany ....... 2901136

[51] Int. Cl.³ .............................................. A61C 3/06
[52] U.S. Cl. ...................................... 433/82; 433/125; 222/105; 401/183
[58] Field of Search ...................... 433/125, 87, 82, 85, 433/89, 90; 15/28; 128/62 A; 222/105, 106, 92, 94, 325; 401/152, 156, 183

[56] References Cited

U.S. PATENT DOCUMENTS

| | | | |
|---|---|---|---|
| 2,652,949 | 9/1953 | Martin | 401/152 |
| 2,838,837 | 6/1958 | Terry | 433/82 |
| 2,841,806 | 7/1958 | Blasi | 128/62 A |
| 3,362,586 | 1/1968 | Dedoes | 222/106 |
| 3,389,468 | 6/1968 | Lewis et al. | 433/82 |
| 3,459,343 | 8/1969 | Rasmussen | 222/325 |
| 3,775,849 | 12/1973 | Condon | 433/125 |
| 3,977,083 | 8/1976 | Leslie et al. | 433/82 |
| 3,977,084 | 8/1976 | Sloan | 433/131 |
| 4,018,361 | 4/1977 | Fegley | 222/325 |
| 4,021,920 | 5/1977 | Kirschner et al. | 433/82 |
| 4,173,828 | 11/1979 | Lustig et al. | 433/87 |

Primary Examiner—Gene Mancene
Assistant Examiner—John J. Wilson
Attorney, Agent, or Firm—Herbert L. Lerner; Laurence A. Greenberg

[57] ABSTRACT

Hand-operated instrument for dental care or tooth treatment having an electric drive, including a hand-grip portion, a slender instrument neck portion having one end integral with the hand-grip portion and a free end, a drive motor of the electric drive and a fluid reservoir disposed in the hand-grip portion, a working implement integral with the free end of the neck portion, means including a fluid duct at least partially disposed in the neck portion for supplying fluid from the reservoir to the working implement, and means including drive elements at least partially disposed in the neck portion and being driven by the drive motor for driving the working implement.

5 Claims, 3 Drawing Figures

U.S. Patent  Feb. 16, 1982  4,315,741
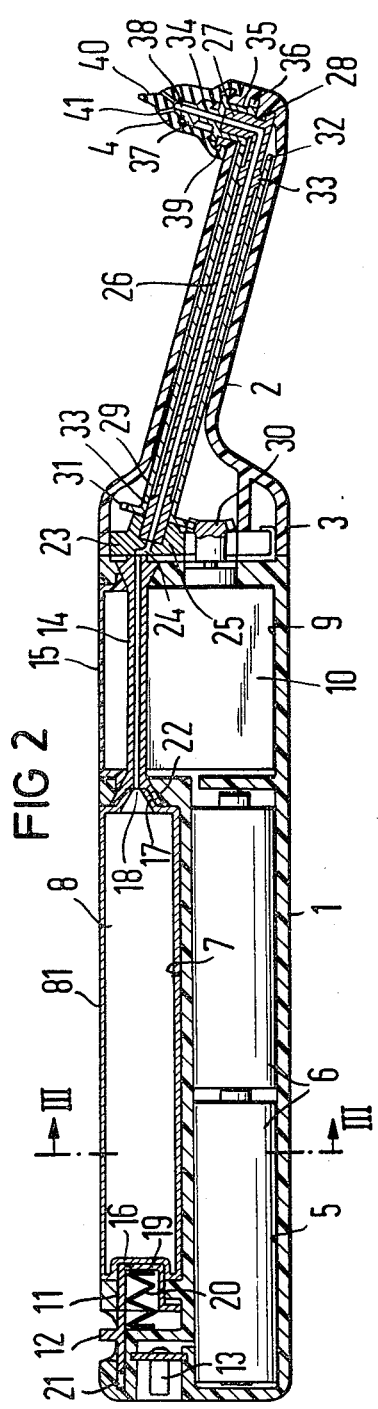
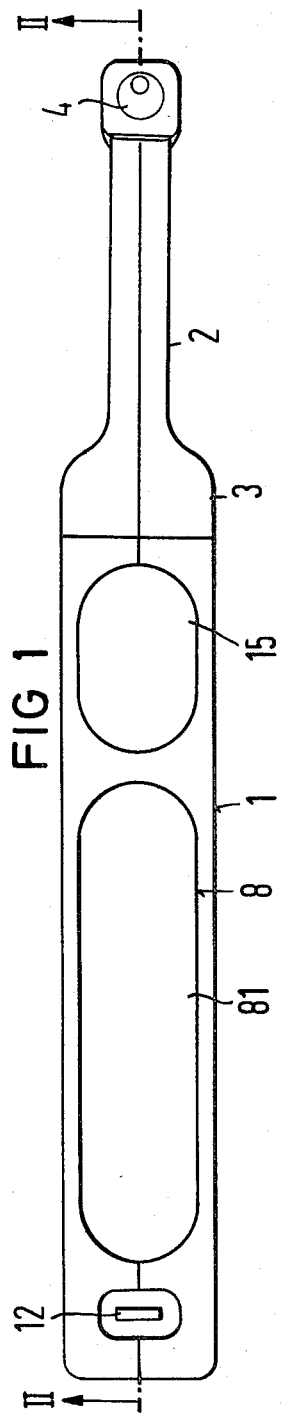
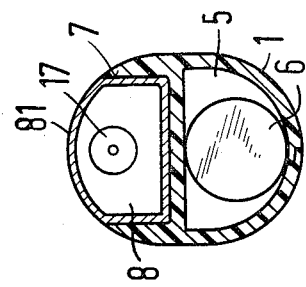

HAND-OPERATED INSTRUMENT FOR DENTAL CARE OR TOOTH TREATMENT

The invention relates to a hand-operated instrument for dental care or tooth treatment with an electric drive, preferably having several different treatment implements or tools which can be coupled to it, and having a fluid reservoir from which the treatment fluid, such as a cleaning fluid, for example, can be directly supplied to the working implement.

It is known to use hand-operated instruments for dental treatments, particularly for the care of teeth wherein brushes, grinding discs or polishing means made of rubber are given rotary motion, in order to clean and treat the surface of the teeth particularly thoroughly. Generally, the drive of such instruments and that of the implements connected to them, is effected by an electric motor, which can be supplied by the line current or possibly by rechargeable batteries. In a known instrument, which is described in U.S. Pat. No. 3,029,451, an implement is disclosed for tooth treatment which can also be used for cleaning teeth and for rubber message, whereby the implement is made to rotate by a drive shaft. In another known instrument disclosed in U.S. Pat. No. 3,802,420, several different work-heads can be exchanged in the instrument. Finally, it is also suggested to construct an instrument of the hereinafore mentioned type in such a manner that a cleaning fluid can be directly supplied to the working implement which is used on the instrument head.

It is accordingly an object of the present invention to provide a hand-operated instrument for dental care or tooth treatment which overcomes the hereinafore mentioned disadvantages of the heretofore known devices of this general type, and in which fluid is supplied to the respective treatment implements in such a manner, that the resulting instrument has a simplified construction and has dimensions which are practical for hand operation.

With the foregoing and other objects in view there is provided, in accordance with the invention a hand-operated instrument for dental care of tooth treatment having an electric drive, comprising a hand-grip portion, a slender instrument neck portion having one end integral with the hand-grip portion and a free end, a drive motor of the electric drive and a fluid reservoir disposed in the hand-grip portion, a working implement integral with the free end of the neck portion, means including a fluid duct at least partially disposed in the neck portion for supplying fluid from the reservoir to the working implement, and means including drive elements at least partially disposed in the neck portion and being driven by the drive motor for driving the working implement. In this way, all the parts of the instrument with relatively large volume i.e. the drive motor and the reservoir for the fluid, are disposed in the thick and corresponding easily holdable hand-grip-part, where they are also easily operated with respect to switching on the drive motor and operating the fluid transport element.

The drive elements for driving the working implements and the lines for supplying the fluid to the implement are disposed in the slender neck of the instrument, since they do not harm the appearance of the instrument and permit an extremely slender neck and thereby an excellent applicability of the instrument even for teeth in the posterior regions of the mouth in that position.

In accordance with another feature of the invention, there are provided means for attaching other implements to the free end of the neck portion in place of the working implement.

In accordance with a further feature of the invention, the drive elements include a tubular drive shaft, the fluid duct being disposed in the tubular drive shaft, and including an implement coupling for coupling the working implement to the free end of the neck portion, and a miter gear connecting the implement coupling to the drive shaft. This permits a particularly slender construction of the instrument neck. Great construction simplification and room saving can be achieved according to further embodiments of the invention as follows.

In accordance with an added feature of the invention, the fluid duct is tubular in shape and the drive shaft is rotatably supported on the fluid duct.

In accordance with an additional feature of the invention, the fluid duct has a bend formed therein which forms a bearing for the miter gear at the implement coupling.

The operation of the hand-operated instruments i.e. the operation of the means for supplying the fluid, according to the invention, are improved since, in accordance with yet another feature of the invention, the fluid reservoir is at least partly formed of manually elastically compressible material.

In accordance with a concomitant feature of the invention, the fluid supplying means includes a supply duct for carrying fluid from one end thereof disposed at the reservoir to another end thereof disposed at the fluid duct, and a funnel-shaped receptor formed in the one end of the supply duct, the reservoir includes a conically tapered tip being at least partially insertable in the funnel-shaped receptor, and the hand-grip portion includes spring-loaded hand-operated detent means for pressing the conically tapered tip against the funnel-shaped receptor portion.

Other features which are considered as characteristic for the invention are set forth in the appended claims.

Although the invention is illustrated and described herein as embodied in a hand-operated instrument for dental care or tooth treatment, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings, in which:

FIG. 1 is a diagrammatic top plan view of the hand-operated instrument according to the invention;

FIG. 2 is a cross-sectional view representation of the hand-operated instrument, taken along the line II—II in FIG. 1, in the direction of the arrows; and FIG. 3 is a sectional view of the hand-operated instrument, taken along the line III—III in FIG. 2, in the direction of the arrows.

Referring now particularly to FIGS. 1-3 of the drawing, it is seen that the outer appearance of the hand-operated instrument for tooth care and tooth treatment is formed by an elongated, cylindrical housing 1 made of plastic, which represents the grip part of the instrument, and which can include two parts. A slender instrument neck 2 is connected to the housing 1, whereby the instrument neck 2 which also includes two parts is provided with a flange part 3, that is preferably in a detachable connection with the cylindrical housing 1. At the free end of the instrument neck 2, a treatment implement 4 formed of rubber, for example, is attached and arranged at a right angle.

In the housing 1, i.e. in the grip of the hand-operated instrument, there is formed a hollow space 5 containing a battery set 6; a hollow space 7, shown open at the top in FIG. 2, containing a fluid receptacle 8; another hollow space 9 containing an electric drive motor 10 which is connectible to the battery set 6; a detent element 11, to be further explained hereinbelow, with an operating lever 12; an electric connector 13 for the electrical connection of the battery set 6 to a recharger of known construction; and also a cylindrical supply duct 14 for the fluid which is disposed near the drive motor 10. This portion of the housing can be closed by a snap-in cover 15.

The fluid reservoir 8 has an arched upper surface 81 made of an elastically deformable and compressible material. Furthermore, the fluid reservoir 8 is provided with a detent recess 16, and at its other end it has a conically tapering tip 17 which forms the fluid-discharge orifice 18.

The hereinafore mentioned detent element 11 is made as a formed part having several bends, and being provided with the operating lever 12 and with a detent projection 19 which fits into the detent recess 16 and is slidable to the left in guide slots 21 of the housing 1 against the force of a spring 20, as shown in FIG. 2. In this way, when the detented connection is released, the fluid reservoir 8 can be removed from the housing 1. In the inserted state, the conical tip 17 of the fluid reservoir 8 is pressed against the inner surface of a funnel-shaped receptor portion 22 of the fluid supply duct 14 so that a leakproof seal is formed.

Inside of the flange part 3 of the instrument neck or instrument head 2, a holder 23 is disposed. The holder 23 comprises a channel 24 for the fluid, and also an opening 25 for an elongated fluid-duct 26 which is disposed at a slight angle with respect to the cylinder axis of the housing 1, in a similar way to the slender instrument neck 2 itself.

As it is clearly shown in FIG. 2, the elongated tube-shaped fluid duct 26 has at one end thereof a right-angle bend 27. The duct 26 also has a channel for the fluid which extends throughout its entire length, the channel being connected with the fluid reservoir 8 by way of the supply duct 14. The fluid duct 26 is positively locked (form-lockingly arrested) by a projection 28 at the free, bent end of the instrument neck 2. A tubular drive shaft 29 is rotatably supported on the fluid duct 26. The drive shaft 29 has a lesser diameter at its middle portion and gear teeth 31 at one end thereof. The gear teeth 31 mesh with a drive pinion 30 of the drive motor 10. The other end of the drive shaft 29 is provided with radial teeth 32. The fluid duct 26 has bearing surfaces designated with reference numeral 33, for supporting the drive shaft 29. The bent portion 27 of the fluid duct 26 forms the bearing for an implement coupling 34 which has a bearing sleeve 35 with a toothed ring 36. A wobble disc 37 and a channel 38 for the fluid in its center is provided on a part which extends beyond the free end of the instrument neck 2. The hereinafore mentioned treatment implement 4 can be mounted onto the last-mentioned freely extending part, and onto the wobble disc 37, whereby the treatment implement is form-lockingly connected, so that no rotation is possible. This is done with the essentially square end portion of the instrument neck by detent means 39. In the region of a wart-like treatment point 40, the treatment implement 4 is provided with several radial channels 41 for the fluid, which are directed toward the treatment zone. The radial teeth 32 of the drive shaft 29, together with the gear teeth 36 of the implement coupling 34, form a miter gear drive, while the combination of the parts 30, 31, 32 and 36 represents a reduction gear drive. By turning on the drive motor 10 by a switch which is not shown, the drive shaft 29 and thereby the implement coupling 34 as well, are made to rotate. Thereby, the wobble disc 37 also rotates and causes a back and forth oscillating motion of the treatment point 40 which is made possible by the elastic yielding property of the detent means 39. Because of the pressure on the upper side 81 of the fluid reservoir 8, the treatment liquid or medication such as a cleaning agent, for example, is first pressed into the supply duct 14 and then into the fluid duct 26, over the fluid channel 38 in the implement 34, and is directly transported to the treatment region through the channels 41. A non-illustrated check valve prevents air or saliva of the person treated from entering into the fluid line when the pressure on the fluid reservoir is removed. By the special configuration and construction of the fluid reservoir 8 and the fluid lines, in conjunction with the special construction and disposition of the drive elements for the treatment implement 4, it is possible to give the instrument neck 2 a very slender form, so that treatment in the mouth at difficult-to-reach points does not present a problem. Furthermore, the construction of the instrument is greatly simplified, particularly in the neck region 2, by the special integration of drive shaft 29 and fluid-duct 26.

There are claimed:

1. Hand-operated instrument for dental care or tooth treatment having an electric drive, comprising a hand-grip portion, a slender instrument neck portion having one end integral with said hand-grip portion and a free end, a drive motor of the electric drive and a fluid reservoir disposed in said hand-grip portion, a working implement integral with said free end of said neck portion, means including a fluid duct at least partially disposed in said neck portion for supplying fluid from said reservoir to said working implement, means including drive elements at least partially disposed in said neck portion and being driven by said drive motor for driving said working implement, said drive elements including a tubular drive shaft, and said fluid duct being disposed in said tubular drive shaft, an implement coupling for coupling said working implement to said free end of said neck portion, and a miter gear formed of two gears connecting said implement coupling to said drive shaft, said fluid duct being tubular in shape and said drive shaft being rotatably supported on said fluid duct, and said fluid duct having a bend formed therein which forms a bearing for both gears of said miter gear at said implement coupling.

2. Hand-operated instrument according to claim 1, including means for attaching other implements to said free end of said neck portion in place of said working implement.

3. Hand-operated instrument according to claim 1, wherein said fluid reservoir is at least partly formed of manually elastically compressible material.

4. Hand-operated instrument according to claim 3, wherein said fluid supplying means includes a supply duct for carrying fluid from one end thereof disposed at said reservoir to another end thereof disposed at said fluid duct, and a funnel-shaped receptor formed in said one end of said supply duct, said reservoir includes a conically tapered tip being at least partially insertable in said funnel-shaped receptor, and said hand-grip portion includes spring-loaded hand-operated detent means for pressing said conically tapered tip against said funnel-shaped receptor portion.

5. Hand-operated instrument according to claim 1, wherein said fluid duct is continuous and uninterrupted.

* * * * *